United States Patent [19]
Kritzinger et al.

[11] Patent Number: 5,755,700
[45] Date of Patent: May 26, 1998

[54] CORNEAL IRRIGATION CANNULA AND METHOD OF USING

[75] Inventors: Michiel S. Kritzinger, 26 Wexford Avenue, Westcliff, Johannesburg, South Africa; Stephen A. Updegraff, 1635 N. Grand Vista Ct., Rapid City, S. Dak. 57701

[73] Assignees: Michiel S. Kritzinger, Johannesburg, South Africa; Stephen A. Updegraff, St. Petersburg, Fla.

[21] Appl. No.: 561,744

[22] Filed: Nov. 22, 1995

Related U.S. Application Data

[60] Provisional application No. 60/001,592 Jul. 27, 1995.

[51] Int. Cl.$^6$ .................................................. A61M 5/00
[52] U.S. Cl. ........................ 604/257; 604/264; 604/35
[58] Field of Search ........................ 604/19, 21, 48, 604/73, 93, 131, 264, 289–90, 294, 296, 280, 257; 606/107, 162

[56] References Cited

U.S. PATENT DOCUMENTS

| | | | |
|---|---|---|---|
| 1,626,839 | 5/1927 | Kallmeyer | 604/264 |
| 3,818,913 | 6/1974 | Wallach | 128/305 |
| 4,357,941 | 11/1982 | Golubkov et al. | 128/316 |
| 4,406,285 | 9/1983 | Villasenor et al. | 128/305 |
| 4,417,579 | 11/1983 | Soloviev et al. | 128/303 R |
| 4,445,897 | 5/1984 | Ekbladh et al. | 604/280 |
| 4,515,157 | 5/1985 | Feforov et al. | 128/303 R |
| 4,523,920 | 6/1985 | Russo | 604/280 |
| 4,705,035 | 11/1987 | Givens | 128/303 R |
| 4,722,724 | 2/1988 | Schocket | 604/294 |
| 4,739,761 | 4/1988 | Grandon | 128/305 |
| 4,744,360 | 5/1988 | Bath | 128/303.1 |
| 4,865,586 | 9/1989 | Hedberg | 604/93 |
| 4,963,142 | 10/1990 | Loertscher | 606/14 |
| 5,147,334 | 9/1992 | Moss | 604/264 |
| 5,226,905 | 7/1993 | Hanna | 606/166 |
| 5,250,062 | 10/1993 | Hanna | 606/166 |
| 5,312,330 | 5/1994 | Klopotek | 604/49 |
| 5,314,439 | 5/1994 | Sungita | 606/166 |
| 5,342,378 | 8/1994 | Giraud et al. | 606/166 |
| 5,383,866 | 1/1995 | Chang | 604/280 |
| 5,407,441 | 4/1995 | Greenbaum | 604/280 |
| 5,626,559 | 5/1997 | Soloman | 604/289 |

FOREIGN PATENT DOCUMENTS

| | | | |
|---|---|---|---|
| 2541919 | 3/1977 | Germany | 604/280 |

*Primary Examiner*—Mark Bockelman
*Assistant Examiner*—Ellen Tao
*Attorney, Agent, or Firm*—Wood, Herron & Evans, L.L.P.

[57] ABSTRACT

A corneal irrigation cannula is used in tectonic lamellar keratoplasty. The cannula is hand manipulatable and allows for entry into the interface of a corneal flap or cap and a corneal bed for the delivery for irrigating fluid under low flow through a plurality of irrigating ports thereby irrigating the interface by gently elevating the overlying cap or flap and washing residual debris from the corneal bed.

15 Claims, 1 Drawing Sheet

CORNEAL IRRIGATION CANNULA AND METHOD OF USING

RELATED APPLICATIONS

This application is a continuation of Provisional Application Ser. No. 60/001,592, filed Jul. 27, 1995, which is incorporated herein in its entirety by reference. This application is also related to applications Ser. Nos. 08/561,541, 08/562,257, and 08/562,253, filed on even date herewith, all still pending, and entitled, "Corneal Surface Marker and Marking Method for Reducing Irregular Astigmatism During Lamellar (LASIK) Corneal Surgery", "Corneal Flap/Cap Elevator" and, "Method for Reducing Irregular Astigmatism and Debris/Epithelium in the Interface During Lamellar Corneal Flap/Cap Surgery", respectively, which are incorporated herein in their entireties by reference.

BACKGROUND OF THE INVENTION

Lamellar corneal surgery has undergone a steady evolution over the last 50 years. Advancements in the technology, such as automated keratomes and non-freeze, no-suture techniques have markedly improved safety and effectiveness. During the surface ablation craze of the late 80's, Dr. Gholam Peyman, known for his pioneering retina work, realized the utility of preserving all layers of the cornea but taking advantage of the extreme accuracy of the excimer laser. He patented the method for LASIK (laser assisted in situ keratomileusis) years ago and studied this technique in his laboratory. He used a YAG laser due to the limited response and acceptance for this technique by the major excimer laser manufacturers. During the years of epikeratoplasty others such as Drs. Lee Nordan and Stephen Slade, as well as Dr. Casimir Swinger were learning and developing freeze myopic keratomileusis for high myopia. By the late 80's, Dr. Slade was one of a hand full of surgeons still performing this demanding technique. When Dr. Luis Ruiz introduced the automated keratome and the in situ non-freeze, no-suture technique to the lamellar bed, Dr. Slade embraced this and has since introduced this technique to thousands of surgeons worldwide. Although a significant advancement, even Dr. Luis Ruiz realized the relative imprecision of making a refractive pass with the keratome. He quickly learned to utilize the excimer laser to precisely reshape the cornea underneath the lamellar corneal flap. The precision achieved has been unparalleled, especially for the moderate to higher myopes.

Worldwide there have been many other surgeons that deserve credit for pursuing the combination of excimer laser with lamellar surgery, most notably Dr. Lucio Buratto of Milan, Italy, and Dr. Ioannis Pallikaris of Greece. The original Buratto technique, however, required cutting a very thick cap and ablating its under surface. Many of these lenticules required suturing, thus required extreme surgical precision and irregular astigmatism rates were quite high. Pallikari' early work was done on animal models and provided the first histopathology of excimer laser to a lamellar bed. The early Summit excimer laser studies that evaluated the use of lamellar surgery were conducted by Brink et al.; however, there was a significant loss of best corrected visual acuity and a wide range of outcomes as new surgeons attempted to perform the original suture dependent Burrato technique.

As surgeons began doing lamellar surgery, they became concerned about the potential for inducing irregular astigmatism as well as introducing debris such as epithelial inclusions in the interface. Fortunately, with the introduction of the automated keratome and non-freeze, non-suture techniques, irregular astigmatism rates are reduced. Debris in the interface, however, continues to be a chronic problem. Many surgeons have resorted to never wearing gloves during lamellar surgery just for that reason. Although infections in lamellar surgery are quite low, when you are the patient that has the infection, percentages do not matter. At present, it is unclear whether or not wearing gloves during lamellar surgery is the standard of care. Thus, we need a way to perform lamellar surgery with gloves safely so as not to introduce debris into the interface.

Recently a very famous clinical researcher in excimer laser technology expressed that his job is now to make surface ablation PRK (photorefractive keractomy) as good or better than LASIK. Preserving all the layers of the cornea provides quicker visual recovery and the predictability is less dependent upon the ablation characteristics of the laser. Thus, LASIK in its infancy already has a head start over any surface ablation technique. Secondly, PRK retreatment is not predictable, LASIK enhancement is possible. The tremendous amounts of research and development required to create the perfect surface ablation could be better spent in perfecting LASIK for all ranges of refractive errors.

There is a growing need to introduce lamellar surgery skills to surgeons new to this arena. Surgeons who have been performing ALK (automated lamellar keratoplasty) will be prepared to make an easy transition to LASIK. Many of the surgeons making the transition from PRK to LASIK appear totally consumed in what type of ablation to use in the bed, when in reality their primary concerns should be a safe keratectomy and repositioning the cap/flap so that there is the least likely chance for debris in the interface or irregular astigmatism. If that can be reproduced, then enhancement is possible and predictability of the ablation for each surgeon will increase with experience.

Several patents disclose devices which utilize irrigation or have specific irrigation conduits for removing debris or tissue from the altered area during opthalmologic surgery. These patents are disclosed herein for convenience, but such disclosure does not mean these patents are the only, or even relevant, patents. For example, U.S. Pat. No. 3,818,913 discloses a surgical apparatus for removal of defective or unwanted tissue is from the lens of an eye. The apparatus employs a high velocity liquid jet conduit which disintegrates the tissue and the debris is subsequently removed by a suction conduit. U.S. Pat. No. 4,744,360 describes a method and an apparatus for ablating and removing cataracts. The apparatus includes an optical fiber, an aspirator sleeve and an irrigation sleeve. The irrigation sleeve and the aspirator sleeve conduct irrigating liquid to and remove ablated material from the anterior chamber. U.S. Pat. No. 4,963,142 discloses a method and apparatus for performing endolaser microsurgery where the laser is coupled to a probe which also houses a coaxial canal for aspiration of tissue and/or fluid. The probe is used solely as an intraocular device. U.S. Pat. No. 5,407,441 describes an opthalmologic cannula for administering anesthetic to the eye.

Notwithstanding developments in opthalmologic lamellar surgery to date, techniques and instrumentation are needed to positively impact all lamellar surgeons who have grappled with sight-threatening irregular astigmatism and debris in the interface.

SUMMARY OF THE INVENTION

This invention is directed to a number of improvements in instrumentation and surgical techniques for reducing irregular astigmatism and debris/epithelium in the interface during lamellar corneal surgery. More particularly, a corneal irrigation cannula for use in tectonic lamellar keratoplasty and a method of using the cannula is provided by this invention.

The corneal irrigation cannula for use in tectonic lamellar keratoplasty comprises a hand manipulatable tub e having one end for receiving an irrigation fluid and an outlet end for delivery of the fluid therethrough. The tube is of sufficient length allowing for entry into the interface of the corneal flap or cap and a corneal bed formed by surgical dissection of the corneal surface. The tube is preferably angled to facilitate entry into the interface. The cannula has an outlet end having a plurality of irrigating ports for the low flow delivery of suitable fluid therethrough to the corneal bed or other area to be irrigated. One of the ports is situated at the tip of the end for delivery of the fluid directly outward from the end while the other ports are situated superiorly and inferiorly thereby directing fluid upward and downward from the ports. The method of using the cannula comprises inserting the outlet end of the cannula into the interface of an overlying corneal cap or flap and corneal bed for the delivery of suitable fluid under low flow or velocity through irrigating ports of the cannula thereby irrigating the interface by gently elevating the overlying cap or flap and washing residual debris and epithelium from the corneal bed. Preferably, the delivery flow of the fluid is from the center of the corneal bed and moves peripherally toward the edge of the bed and cap or flap.

These and other advantages of the present invention will become more apparent from the drawings and detailed description.

DETAILED DESCRIPTION OF THE INVENTION

I. OVERVIEW OF THE SURGICAL PROCEDURE (LASIK)

Figure 1:
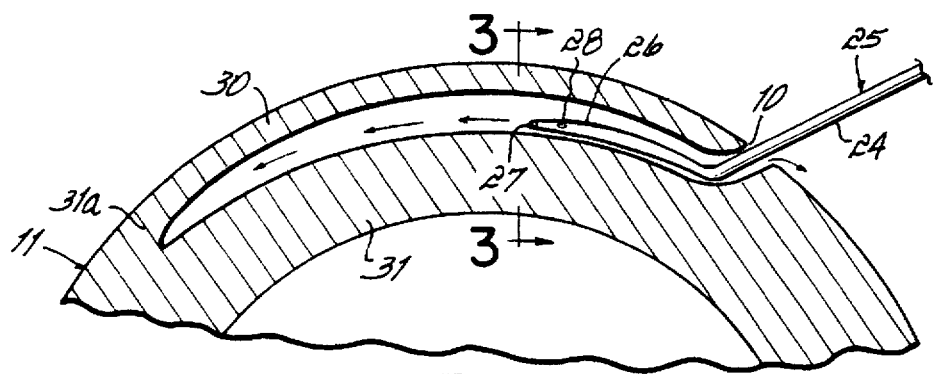
FIG. 1 illustrates a side view of an irrigation cannula of the present invention engaging the interface of the corneal flap and stromal bed with an angled stem.

Prior to a lamellar dissection, a marker is used to outline the present anatomical surface of the cornea. Once the lamellar dissection is made and it is appropriate to return the corneal cap/flap, the corneal bed is irrigated with low flow. The flap/cap is returned. Fluid is aspirated from the fornices such that fluid flows from the bed (top of the dome of the eye) out and downward to the fornices. This first step removes debris and epithelium from the interface. Irrigation should start centrally and move peripherally. The second step requires the suction cannula or aspirator to be placed gently on the edge of the keratectomy to prevent debris/ epithelium from wicking back under the flap/cap. With a layer of irrigation fluid in the interface, the corneal flap/cap is then aligned with the preoperative surface marking. If debris continues to be present or the cap is not aligned, the method is repeated.

A. Preoperative ALK or LASIK

1. Eye Prep

We recommend mild lid scrubs to the eyelid margins. Patients diagnosed with meibomianitis or blepharitis should be adequately treated prior to surgery. This may include a short term use of systemic Tetracycline to help reduce meibomian secretions prior to surgery. Be sure to confirm that the patient is not pregnant and is not planning to become pregnant over the next six months as this may affect the outcome of the surgery.

2. Irrigation of the Fornices

A thorough irrigation of the inferior fornices and glove with cool BSS (balanced salt solution) should be conducted. As many have noticed for a long time during cataract surgery when meibomian secretions are present as a layer in a pool of irrigating solution, a quick irrigation and aspiration with the head tilted will remove this oily film in a large sheet. This is what we believe is happening when they tilt the patient's head and have already done the lid scrubs and irrigate the fornices. Thus, meibomian secretions are not present during the keratectomy.

3. Eye Drops a. Pilocarpinte 2% is used before the marking ring over the constricted pupil.

b. Light Reflex Constriction

This can be a little more difficult for patients to fixate. It prevents pharmacologic decentration of the pupil and probably is the most accurate way to achieve centration over the entrance pupil.

B. Operative

1. Draping

This is one of the most important steps. Whatever operative protective cover or drape you plan to use, it must retract the eyelashes out of the field and the drape should not restrict the speculum from opening fully so that adequate exposure of the globe can be obtained for suction. We presently use a 10–24 drape made by 3M to accomplish this.

2. Irrigation System

At present, we have been using the roller clamp on the IV bottle to control the flow of the BSS Plus through the irrigation cannula. We have found that it is best if this flow is just adequate to float a cap or flap off the bed without creating distortions, undulations or undue turbulence. This irrigation can also be used to irrigate the globe and cornea prior to surgery.

3. LASIK Marking System

Lamellar corneal surgery has undergone many changes in instrumentation and technique. The most recent advancement is excimer laser in situ keratomileusis or LASIK. This is a non-freeze, non-suture technique that incorporates the precise reshaping of the corneal stroma with the laser and the minimal wound healing/quick recovery of lamellar corneal surgery. A major complication, which can be sight threatening of lamellar corneal surgery is irregular astigmatism.

To date, corneal surgeons have used subtle and often imperceptible visual cues to reapproximate the flap or corneal tissue. It is apparent that a slight decentration or disorientation of the flap can result in irregular astigmatism. We propose the concept of a corneal surface marker, the Kritzinger-Updegraff (KU) LASIK marker, to improve centration of the procedure and the precise repositioning of the corneal cap or flap. This marker was developed to permit a centered keratectomy which is dependent upon an outer ring on which the surgeon centers the suction ring. The marker also has six radial and two pararadial marks within it. These radial marks vary in width which permits precise repositioning of the cap or flap edges. This prevents microdecentration seen when the surgeon uses an equally gapped gutter as the cue for alignment. The pararadial marks aide in preventing a reversed free cap.

The corneal surface marker consists of two concentric rings; one 5 mm in diameter with cross-hair (to aid centering) and 10 mm to 10.5 mm in diameter radiating off the center ring are six radial and two pararadial marks. The width of the superior and inferior radials as well as one temporal pararadial are two times thicker than the other radials. The pararadials at 11:00 and 1:00 are of different width to ensure proper orientation of a free cap and prevent placement of a free cap upside down (epithelial surface down). The concentric rings ensure centration of the mark and subsequent centration of the LASIK suction ring. The different widths of the pararadials and radials permit accurate, anatomic repositioning of the cap or flap with microsurgery. The radiating marks extend beyond the outer ring to provide adequate reference points with the large flaps made with the LASIK suction ring.

4. Centration a. Positioning the Patient's Head

The goal is to have the globe absolutely centered in the patient's socket as the patient fixates on the red fixation beam. An attempt should be made to position the patient's chin and forehead so that the globe is on a flat plane. It is important to make sure that the chin cannot move up or down and the head must be stable so that it cannot turn left or right. Once you have the globe centered within the orbit and looking straight ahead, use the joy stick of the X axis to bring the patient "dead" center in the cross-hairs that are in the optics of the right eye piece. The KU corneal marker is then positioned so that the superior and medial lateral marks of the cross-hair match with those of the marker. Thus, after creating the mark the cross-hairs can be superimposed upon it. If there is not absolute correspondence of the cross-hairs in the mark that is placed on the cornea, the surgeon is then responsible to make a "mental note" of this orientation when ablating the stromal bed and putting the flap back into position. At this point with the Keracor 116 laser, the red and green light must be superimposed prior to placing these marks or the cross-hair will move away from the center of the pupil after these maneuvers have been performed.

b. Applying the Suction Ring

It is important to have the circular mark of the KU marker aligned concentrically with the suction ring. This ensures that the flap will be central to the pupil.

c. Ablation

After the keratectomy is performed, the flap is folded back nasally. The peripheral markings of the KU marker are still visible. Thus, these are used as a visual cue to line up the cross-hair of the redicule which correspond to the exact fixation prior to the keratectomy. It is very important not to move the joy stick of the excimer laser at this point to center the ablation. Rather, move the patient's head gently to achieve centration. Improper alignment of the patient's head does not mean the bed has moved but rather the patient's head has moved and thus must be oriented back to the position you had initially worked so hard to achieve. Do not play with the joy stick.

d. Added Security Measures

When using the Keracor 116 laser, leave all three lights on; two red lights and one green light. The one red light with a green indicates that as you are lasering you are at the correct level of focus. The other red light follows the actual laser and indicates the orientation of the laser beam whether it is astigmatism or spherical correction. This is an added security measure to ensure that you are lasering the proper axis.

e. Centering Pearl

When you are lasering, turn the light down and ask the patient continuously to look into the red fixation light. This is a cross-check to ensure that the patient is centering on the cross-hair and that the laser treatment is in the center of the pupil. Between each zone of treatment, we recommend either using a regular or special "hockey stick"-shaped to wipe excess fluid from the stromal surface.

f. Addendum to Centration

Eye trackers can be very helpful, however, we feel that these steps in centering the globe are much more fail-safe and ultimately efficient.

5. Suction Rings a. Adjustable Ring

The adjustable suction ring can be used for LASIK, however, this consistently creates a small flap or cap. On average, the diameter is 7.2 mm. For standard ALK cases, we do not recommend routinely trying to use the excimer laser suction ring because the grooves in the sclera that this creates do not match the adjustable suction ring and it can be difficult to center your suction ring for the very critical refractive pass with standard ALK.

b. LASIK Suction Ring

This ring has a larger inside diameter than the adjustable suction ring and it allows the keratome to be exposed to more cornea thus creating keratectomies which are on the average 8.55 mm in diameter. This is the suction ring of choice for LASIK. However, when placing this suction ring on a globe that retropulses fairly freely, it is important to proptose the globe with a speculum so that the suction ring has a firm adherence to the globe prior to initiating suction. Because the outside of the LASIK suction ring is a smaller diameter than the adjustable suction ring, firm pressure on the suction ring handle can retropulse the globe and thus make it difficult to have clearance for the keratome. The adjustable suction ring on the other hand has a large place that will rest on the eyelids and if the globe is proptosed it will be held by the suction of the suction ring and in turn the suction plate will be held upwards by the eyelids providing easier exposure. This will become less of significance as surgeons gain experience with the fixed LASIK suction ring.

6. Ablation

Remember to center with KU marker cues.

II. IRRIGATION CANNULA AND METHOD FOR LOW FLOW TECTONIC LAMELLAR KERATOPLASTY

The present invention and its advantages will be better understood from the above outlined stages of the surgical procedure and the following detailed description incorporating references to the accompanying drawing figures. In the various figures, like reference characters are used to designate like parts.

A. Irrigation Cannula and Technique

With the most recent advancement of excimer laser in situ keratomileusis and its popularization, it has become necessary to develop instruments which will reduce the most significant complications of lamellar surgery: irregular astigmatism and debris/epithelium in the interface. We described above a method and instrument for marking, aligning and returning the overlying corneal flap to its correct anatomical position. We now describe in detail an irrigating cannula and technique that will remove debris from the interface and improve on the problem of postoperative irregular astigmatism stemming from lamellar keratoplasty.

Figure 2:
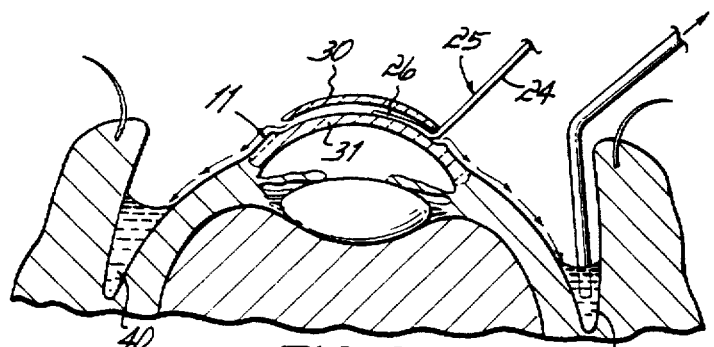
FIG. 2 illustrates a side view of a cannula and irrigation technique of the present invention wherein an irrigation cannula engages the corneal interface and gently lifts the corneal cap from the stromal bed while an aspirating cannula removes the residual fluid and debris that has collected in the fornices after being removed from the corneal interface.

With reference to FIGS. 1 and 2, once the keratectomy is made, an anterior chamber irrigating cannula 25 of the present invention is introduced underneath the flap and into the interface between corneal flap or cap 30 and bed 31. Cannula 25 has an angled stem or handle 24 which enables the introduction into the interface. As previously mentioned briefly and as shown in FIG. 1, the irrigation flow should be adjusted so that the cap/flap 30 floats gently above the bed 31. The goal is to have the patient fixating so that the apex of the globe is in line with the microscope. This allows the fluid to flow from underneath the cap or flap 30 peripherally and out past the limbus into the fornices 40 and 41. The fornices can be aspirated with a low flow aspirating suction cannula 33 (see FIG. 2). This removes epithelial debris and lint from the interface. After approximately 15 to 20 seconds of this form of irrigation, the irrigating cannula 25 can be moved centrally towards the stromal hinge 31a and gently swept back and forth from the hinge 31a and then held centrally again. This allows any epithelium entrapped by the blade at the hinge 31a to be freed and irrigated out. Once the fornices 40 and 41 are cleared of fluid, the aspiration cannula 33 can be moved towards the gutter 10 and with a low flow irrigation, the cap 30 can be nudged so that the radial and pararadial preoperative marks are fairly aligned. Once this is achieved, the gutter 10 should be aspirated 270 degrees while there is steady irrigation (see FIG. 4). This again removes debris that could have hung up at the edge of the keratectomy and not run to the fornices 40 and 41. Aspiration of the gutter 10 is continued as the irrigating cannula is gently withdrawn taking note of the approximation of the radial and pararadial marks.

We are presently using a curved tying forceps to smooth the flap or cap 30 from the center to the periphery in making sure the radial and pararadial marks are aligned. If alignment is not achieved, the irrigating cannula 25 is once again reintroduced and aspiration is performed in the gutter 10 while the cap 30 is allowed to be adjusted on a bed of fluid.

Figure 3:
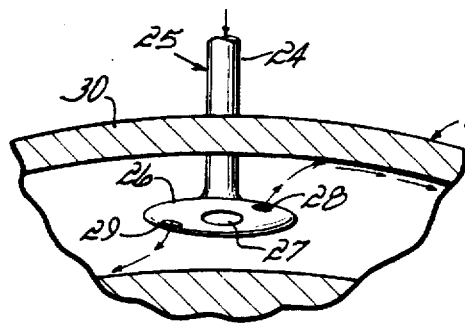
FIG. 3 is a cross-sectional view taken on lines 3—3 of FIG. 1 of the present invention wherein the desired low flow pattern emanating from the angled ports of the cannula gently lifts the corneal flap or cap from the stromal bed and moves debris and particulate to the periphery.
Figure 5:
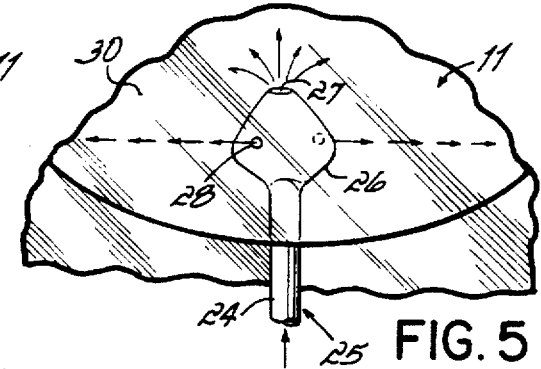
FIG. 5 illustrates an enlarged top view of a cannula of the present invention wherein the flow pattern emanating from a flat tip and angled side ports of the cannula end is demonstrated.

Referring particularly to FIGS. 3 and 5 of the drawings, the cannula shown generally at 25 between corneal flap or cap 30 and the stromal bed 31 has three 25 gauge irrigating ports on its end 26. As shown cannula 25 has a head shaped in cross-section to provide a major axis and a minor axis with at least two irrigating ports, 28 and 29 located along the major axis for directing fluid upward and downward, respectively, as shown. One of these ports, 27, located at the tip of end 26 will deliver low flow irrigating fluid directly from the tip. The other two ports will be approximately 90 degrees away with one, 28, elevated and angled superiorly and one, 29, angled inferiorly. As illustrated in FIGS. 3 and 5, on low flow with balanced salt solution, the irrigating cannula 25 with its unique port configuration generates a flow pattern indicated by arrows that very gently elevates and suspends the overlying corneal flap or cap 30 while washing debris and epithelium to the inferior fornix where it is aspirated with a suction cannula. The constant irrigation of the bed 31 which is at the apex of the dome of the cornea and globe will allow debris to be removed from the interface preventing postoperative irregular astigmatism.

Figure 4:
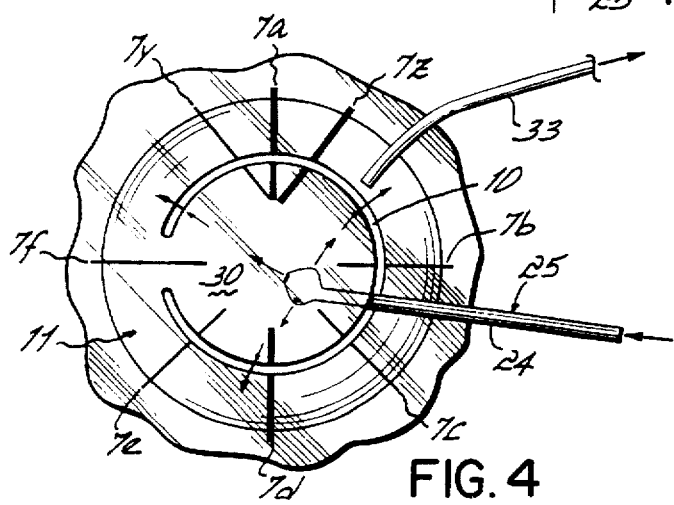
FIG. 4 illustrates a top view of a cannula and the irrigation technique of the present invention eliminating epithelium and debris from the corneal interface and aspirating the residual fluid and debris from the edge of the keratectomy. Also illustrated are preoperative markings on the corneal surface for anatomically aligning the corneal flap or cap correctly.

Referring to FIG. 4, the final maneuver is to aspirate with suction cannula 33 residual fluid from the gutter 10 out of the keratectomy to ensure that no particles will be wicked back into the interface once the fluid has decreased. This is done while the irrigating cannula 25 is delivering low flow fluid from the center of the interface to the periphery (towards the keratectomy).

By utilizing the preoperative markings 7a through 7f and 7y and 7z from the above described Kritzinger/Updegraff LASIK marker and marking method, the cornea is gently massaged with a blunt forceps or a moistened sponge so the cornea is returned into the correct anatomical position. If any wrinkling of the corneal cap or flap is evident or there is not correct alignment of any of the eight (8) radial or pararadial marks, then the irrigating cannula is reintroduced and the cap or flap repositioning procedure is performed again.

In its most preferred form, the irrigating cannula 25 at FIG. 5 is approximately 25 gauge in diameter and most notably has a triangulated flat end 26, the tip of which is blunt. The blunt tip has a port 27, a port 28 coming out from the top of the left sided portion of end 26, and a port 29 (shown in FIG. 3) emanating fluid from the bottom or the right sided portion of the triangulated end 26. This allows flow of fluid not only directly away from the cannula out of port 27, but also up and out from port 28 and down and out from port 29.

This flow pattern from the cannula 25 allows a gentle flow of fluid between the corneal cap or flap 30 and the lamellar bed 31 elevating the cap while cleansing the corneal bed of debris and loose epithelium.

B. Cap/Flap Adherence

1. Use of Air on Corneal Surface

Air blown on the surface of the cornea can be used working from the center of the corneal surface to the periphery for adherence to the cap/flap. This wicks out fluid from the center to the gutter which again improves the removal of debris and epithelial inclusions from the interface. We believe that there is a higher incidence of folds or cracks in Bowman's membrane when air is used. We also believe that using surface air requires one to work very quickly, because the cap will adhere very rapidly, thus it must be well-centered before the air is introduced. Presently, we prefer to use merocel sponges and very carefully use the tip of this to wick the fluid from the gutter and out from underneath the cap/flap. Extreme care must be taken when using the merocel to remove the fluid in that the patient must have solid fixation. If the patient looks into the merocel, the edge of the cap or flap will become bunched up and potentially dislodge the perfect orientation we had previously achieved with the irrigation and aspiration maneuver. However, we do find that with approximately three minutes of time the cap or flap is quite adherent by using this maneuver.

2. Adherence Tests a. Slade Stria Test

By taking a pair of curved tying forceps and gently depressing approximately 1–2 mm away from the keratectomy gutter, one can see folds or stria originating from the point of depression in the cornea up past the gutter and on the surface of the cap or flap. This should be seen for 360 degrees upon depression. If there are no stria two things are occurring, 1) the cap of flap has not adhered to the bed; 2) the cap of flap has possibly folded on itself on the edge and is preventing adherence of the or flap. With the merocel drying technique, we typically place a drop of BSS on the central cornea while drying the gutter. This improves postoperative visual recovery and aids in patient fixation.

b. Blink Test

Have the patient repeatedly blink his or her eyes following the Slade Stria Test to confirm the adherence of the cap or flap. One must be very cautious when removing the 10-24 drape. We typically remove the drape as we remove the lid speculum and that way the lid speculum retracts the drape away from the globe as we move them simultaneously. Caps and flaps have been dislodged upon removing speculums and more likely when the edge of a sharp drape catches the keratectomy of the cap and either totally dislodges it or disorients it so that irregular astigmatism is present after surgery. One should always check with the blink test after the drape is removed.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

We claim:

1. A corneal irrigation cannula for use in tectonic lamellar keratoplasty comprising:

an irrigation fluid source, a hand manipulatable tube of sufficient length allowing for entry into the interface of a corneal cap or flap and a corneal bed formed by surgical dissection, said tube having an inlet end connected to said irrigation fluid source for receiving an irrigation fluid and an outlet end for delivery of the irrigation fluid into said corneal interface, and said outlet end having a head shaped in cross-section to provide a major axis and a minor axis at least two irrigating ports located at said head along said major axis, for the low flow delivery of the fluid therethrough, one of said ports for directing fluid upward and the other port for directing fluid downward for irrigation of said corneal interface to gently elevate and suspend the overlying cap or flap while washing residual debris from said corneal interface.

2. The corneal irrigation cannula of claim 1 wherein said tube is angled to facilitate entry into the interface.

3. The corneal irrigation cannula of claim 1 wherein another port is situated at a tip of said outlet end head for the delivery of fluid directly outward from said outlet end head.

4. The corneal irrigation cannula of claim 1 wherein said one port is angled superiorly and said other port is angled inferiorly on said outlet end head for directing fluid upward and downward from said ports into the interface.

5. The corneal irrigation cannula of claim 4 wherein said superiorly and inferiorly angled irrigating ports are located approximately 180 degrees from each other.

6. The corneal irrigation cannula of claim 4 wherein said superiorly and inferiorly angled ports are located approximately 90 degrees from an irrigating port at the tip of said end.

7. The corneal irrigation cannula of claim 4 wherein another port is situated at a tip of said outlet end head for the delivery of fluid directly outward from said outlet end head.

8. The corneal irrigation cannula of claim 1 wherein said outlet end has a generally flattened triangularly shaped head and has three irrigating ports for delivery of fluid therethrough.

9. The corneal irrigation cannula of claim 8 wherein each of said irrigating ports is approximately 25 gauge in diameter.

10. A corneal irrigation cannula for use in tectonic lamellar keratoplasty comprising:

a hand manipulatable and angled tube of sufficient length allowing for entry into an interface of a corneal cap or flap and a corneal bed formed by surgical dissection, said tube having an inlet end for receiving an irrigation fluid and an outlet end for delivery of the fluid into said corneal a flattened generally triangularly shaped outlet end having a plurality of irrigation ports for the low flow delivery of the fluid therethrough to said corneal interface to gently elevate and suspend the overlying cap or flap while washing residual debris from said corneal interface, one of said ports is situated at the top of the end for the delivery of fluid directly outward from said end and the other ports are angled superiorly and inferiorly for directing fluid upward and downward from said other ports.

11. The corneal irrigation cannula of claim 10 wherein said superiorly and inferiorly angled irrigating ports are located approximately 180 degrees from each other.

12. The corneal irrigation cannula of claim 10 wherein said superiorly and inferiorly angled irrigating ports are located approximately 90 degrees from said irrigating port at the tip of said end.

13. The corneal irrigation cannula of claim 10 wherein said ports are each approximately 25 gauge in diameter.

14. The corneal irrigation cannula of claim 10 wherein said triangularly shaped end has three irrigating ports for delivery of fluid therethrough, one of said ports is situated at the tip of the end for the delivery of fluid directly outward from said end while the other two ports are angled superiorly and inferiorly directing fluid upward and downward from said ports.

15. The corneal irrigation cannula of claim 14 wherein each of said three irrigating ports is approximately 25 gauge in diameter.

* * * * *